(12) United States Patent
Amtmann et al.

(10) Patent No.: US 6,558,520 B2
(45) Date of Patent: May 6, 2003

(54) CIRCUIT CONFIGURATION FOR GENERATING A VIRTUAL GROUND

(75) Inventors: Markus Amtmann, Regensburg; Stephan Bolz, Pfatter; Jürgen Rössler, Münnerstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 2 days.

(21) Appl. No.: 09/781,632

(22) Filed: Feb. 12, 2001

(65) Prior Publication Data

US 2001/0019018 A1 Sep. 6, 2001

Related U.S. Application Data

(63) Continuation of application No. PCT/DE99/02496, filed on Aug. 10, 1999.

(30) Foreign Application Priority Data

Aug. 10, 1998 (DE) ......................... 198 36 129

(51) Int. Cl.⁷ ............................. G01N 27/407
(52) U.S. Cl. ............... 204/425; 204/406; 204/426; 204/427
(58) Field of Search ................ 204/421–429, 204/406

(56) References Cited

U.S. PATENT DOCUMENTS 4,559,126 A * 12/1985 Mase et al.
4,803,866 A    2/1989 Miki et al.

FOREIGN PATENT DOCUMENTS

| DE | 40 35 132 A1 | 5/1992 |
| DE | 197 34 860 A1 | 3/1999 |
| DE | 19836128 A1 * | 2/2000 |
| EP | 0 849 590 A2 | 6/1998 |

OTHER PUBLICATIONS

XP–002128341 is an Abstract from Three–Terminal and Four–Terminal Regulators, 6.19 Switching regulators and dc–dc converters, pp. 355–377;.

* cited by examiner

Primary Examiner—T. Tung
(74) Attorney, Agent, or Firm—Laurence A. Greenberg; Werner H. Stemer; Ralph E. Locher

(57) ABSTRACT

A circuit configuration for generating a virtual ground includes a micro-controller, an analog circuit and a read-only memory. A pulse-width modulated signal, which is output by the micro-controller, is converted, by using the analog circuit, into the virtual ground as a common reference potential of an exhaust probe which operates according to the principle of the galvanic oxygen concentration cell with a solid electrolyte. The actual value of the virtual ground is read into the micro-controller through the use of an A/D converter and is compared with a predefined setpoint value. The potential value of the virtual ground is then controlled on the basis of the difference value. An exhaust probe configuration is also provided.

18 Claims, 2 Drawing Sheets

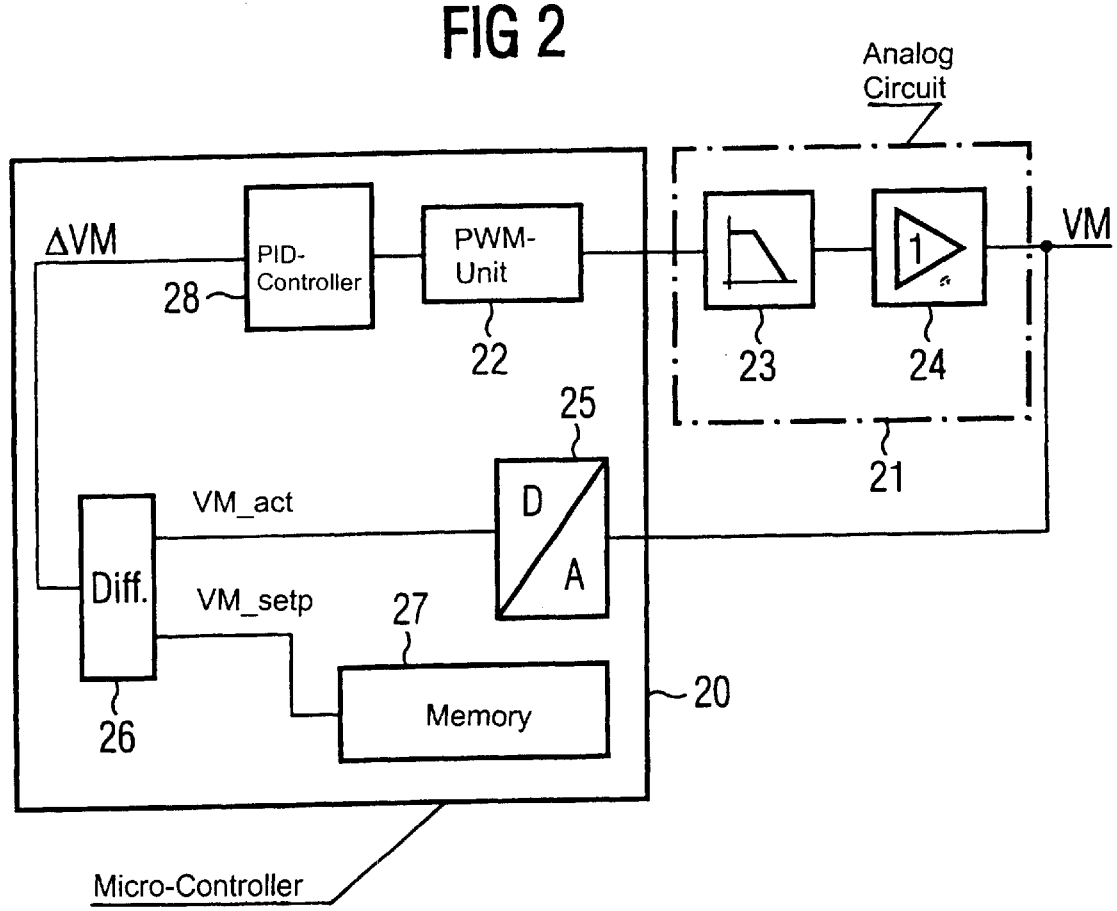

CIRCUIT CONFIGURATION FOR GENERATING A VIRTUAL GROUND

CROSS-REFERENCE TO RELATED APPLICATION

This application is a continuation of copending International Application No. PCT/DE99/02496, filed Aug. 10, 1999, which designated the United States.

BACKGROUND OF THE INVENTION

Field of the Invention

The invention relates to a circuit configuration for generating a virtual ground as a common reference potential for an exhaust gas probe in a motor vehicle.

As environmental awareness is increasing and resulting exhaust gas regulations are becoming increasingly strict, the need to reduce pollutants in exhaust gases of internal combustion engines in motor vehicles is becoming increasingly important. Compliance with currently valid emission limits for pollutants such as carbon monoxide (CO), nitrogen oxides ($NO_x$) and hydrocarbons (HC) requires, on the one hand, selective engine control and, on the other hand, catalytic post treatment of the exhaust gases. For both measures it is necessary to get measurement values with exhaust gas probes—for example lambda probes or $NO_x$ probes.

It is known to use thick film sensors to measure the concentration of pollutants in the exhaust gas of an internal combustion engine. Such a sensor is described, using the example of a $NO_x$, sensor, by N. Kato et al. in the publication "Performance of Thick Film $NO_x$, Sensor on Diesel and Gasoline Engines", Society of Automotive Engineers, Publication 970858, 1997. This $NO_x$ sensor has two measuring cells and three oxygen pump cells and implements the following measuring concept: in a first measuring cell to which the gas to be measured is fed via a diffusion barrier, a first oxygen concentration is set through the use of a first oxygen ion pump current, wherein no decomposition of $NO_x$, occurs. In a second measuring cell, which is connected to the first measuring cell via a diffusion barrier, the oxygen content is further reduced through the use of a second oxygen ion pump current and $NO_x$. is decomposed at a measuring electrode. The oxygen which is generated in this way is used as a measure of the $NO_x$, concentration. The entire $NO_x$, sensor is heated to an increased temperature, for example 700° C., through the use of an electric heating element.

In order to operate such a sensor it is necessary to regulate the respective pump current for the oxygen pump cells precisely. Because motor vehicles generally have an asymmetrical supply voltage, the generation of both positive and negative pump currents requires a reference potential in the center of the supply voltage range.

SUMMARY OF THE INVENTION

It is accordingly an object of the invention to provide a circuit configuration which can generate a virtual ground as a common reference potential.

With the foregoing and other objects in view there is provided, in accordance with the invention, a circuit configuration for generating a virtual ground for an exhaust probe operating according to a principle of a galvanic oxygen concentration cell with a solid electrolyte, including:

a micro-controller for determining an actual value of a virtual ground and generating a pulse-width-modulated signal;

an analog circuit connected to the micro-controller, the analog circuit converting the pulse-width-modulated signal into the virtual ground; and a read-only memory operatively connected with the micro-controller for providing a setpoint value of the virtual ground.

A micro-controller in conjunction with an analog circuit is used to generate the virtual ground. The actual potential value of the virtual ground is read into the micro-controller using A/D converters and compared with a predefined setpoint value. The potential of the virtual ground is regulated to a value in the center of the supply voltage range on the basis of the resulting difference value so that both positive and negative pump currents can be generated. The measuring error of the entire circuit configuration is thus reduced to the errors of the A/D conversion caused by leakage currents and quantization errors.

With the objects of the invention in view there is also provided, an exhaust probe configuration, including:

an exhaust probe having a galvanic oxygen concentration cell configuration with a solid electrolyte;

a circuit configuration connected to the exhaust probe for generating a virtual ground;

the circuit configuration including a micro-controller, an analog circuit and a read-only memory;

the microcontroller determining an actual value of the virtual ground and generating a pulse-width-modulated signal;

the analog circuit converting the pulse-width-modulated signal into the virtual ground; and the read-only memory providing a setpoint value of the virtual ground.

According to another feature of the invention, the read-only memory is a programmable read-only memory.

According to yet another feature of the invention, the read-only memory is integrated into the micro-controller.

According to a further feature of the invention, the micro-controller includes a difference former, a pulse-width modulation unit, and a controller; the difference former forms a difference value from the actual value of the virtual ground and the setpoint value of the virtual ground; the pulse-width modulation unit generates the pulse-width-modulated signal; and the controller controls the pulse-width modulation unit based on the difference value.

According to another feature of the invention, the controller is a PID controller.

According to yet another feature of the invention, the micro-controller has an output impedance; the analog circuit includes a filter circuit and an impedance converter; the filter circuit converts the pulse-width-modulated signal into a DC voltage signal; and the impedance converter adapts the output impedance of the micro-controller.

Other features which are considered as characteristic for the invention are set forth in the appended claims.

Although the invention is illustrated and described herein as embodied in a circuit configuration for generating a virtual ground as a common reference potential for an exhaust gas probe in a motor vehicle, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.
}

BRIEF DESCRIPTION OF THE DRAWINGS

FIG. 2 is a block circuit diagram of the circuit configuration according to the invention for generating a virtual ground.

DESCRIPTION OF THE PREFERRED EMBODIMENTS

Figure 1:
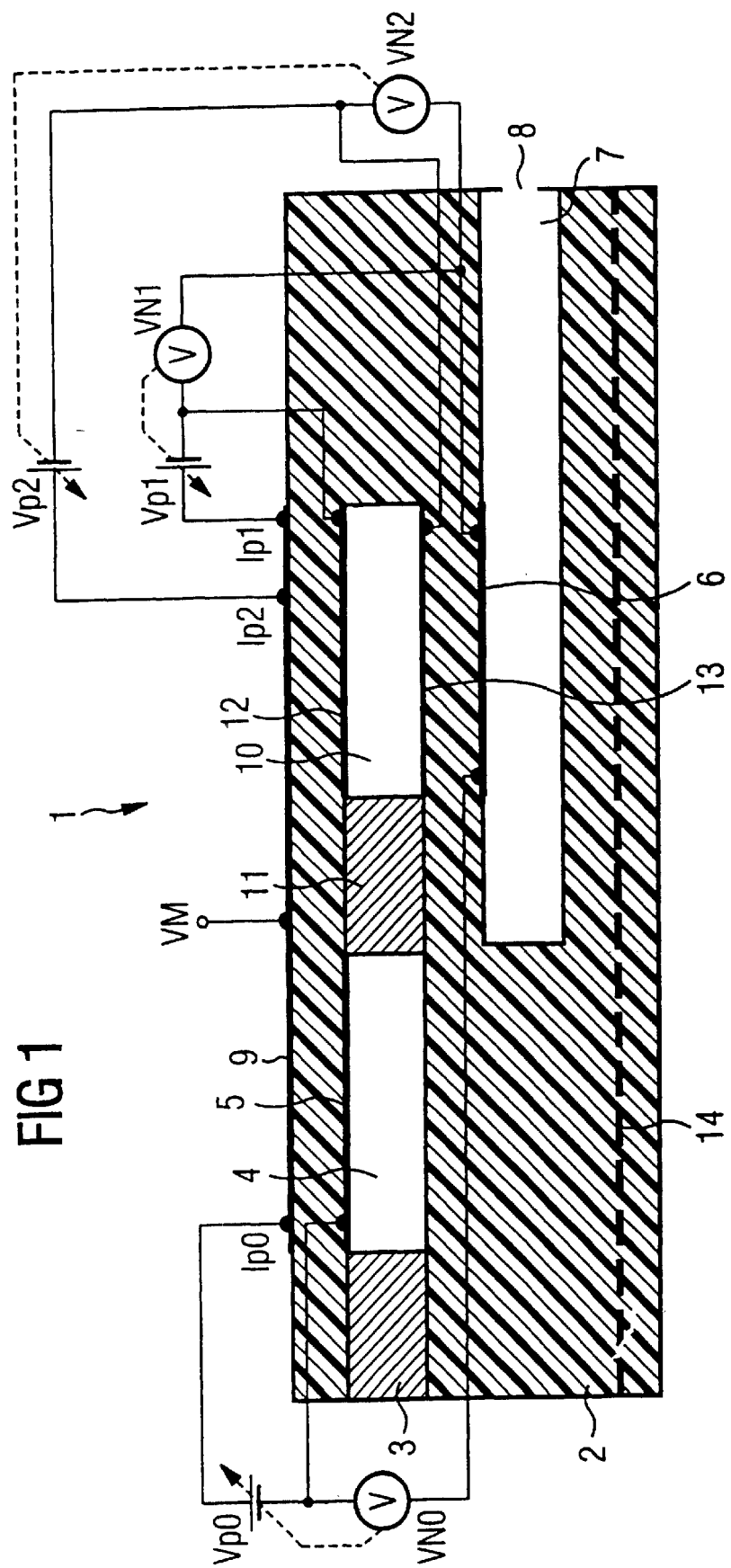
FIG. 1 is diagrammatic sectional view of a $NO_x$ sensor.

Referring now to the figures of the drawings in detail and first, particularly, to FIG. 1 thereof, there is shown a schematic sectional illustration of a $NO_x$ sensor 1. The $NO_x$ sensor 1 which is composed of a solid electrolyte 2, in this case zircon dioxide, receives the gas to be measured via a first diffusion barrier 3. The exhaust gas diffuses through the diffusion barrier 3 into a first measuring cell 4. The oxygen content in this measuring cell is measured from a first Nernst voltage VN0 between a first pump electrode 5 and a reference electrode 6 which is exposed to ambient air. The reference electrode 6 here is provided in an air duct 7 into which ambient air passes via an opening 8. Both electrodes 5, 6 are conventional platinum electrodes.

According to a general method, the measured value of the first Nernst voltage VN0 is used to set a first control voltage or regulating voltage Vp0. The control voltage VpO drives a first oxygen ion pump current Ip0 through the solid electrolyte 2 of the $NO_x$ sensor 1 between the first pump electrode 5 and an external electrode 9 whose potential is at a virtual ground VM serving as a common reference potential—the pump electrode 5 and the external electrode 9 form a first pump cell. Here, the control voltage VpO is set by a controller in such a way that a predefined oxygen concentration is present in the first measuring cell 4.

The first measuring cell 4 is connected to a second measuring cell 10 via a second diffusion barrier 11. The gas present in the measuring cell 4 diffuses into the second measuring cell through this diffusion barrier 11. The second oxygen concentration in the second measuring cell 10 is measured through the use of a second Nernst voltage VN1 between a second pump electrode 12, which is also a platinum electrode, and the reference electrode 6 and used by a controller to set a second control voltage Vp1 which drives a second oxygen ion pump current Ip1. The second oxygen ion pump current Ip1 from the second measuring cell 10 flows from the second pump electrode 12 through the solid electrolyte 2 to the external electrode 9 (second pump cell). The second oxygen ion pump current Ip1 is used to set a predefined oxygen concentration in the second measuring cell 10.

The $NO_x$ concentration which is not affected by the previous processes in the measuring cells 4 and 10 is now determined at a measuring electrode 13 which is configured to be catalytically active. For this purpose, a third oxygen concentration is measured through the use of a third Nernst voltage VN2 between the measuring electrode 13 and the reference electrode 6 and is used by a controller to set a third control voltage Vp2. By applying this control voltage Vp2 between the measuring electrode 13 and the external electrode 9 (third pump cell), the $NO_x$ is decomposed and the released oxygen is pumped through the solid electrolyte 2 in a third oxygen ion pump current Ip2 to the external electrode 9. When the residual oxygen content in the measuring cell 10 is sufficiently low, the third oxygen ion pump current Ip2 is conducted only by oxygen ions which originate from the decomposition of $NO_x$. It is thus a measure of the $NO_x$ concentration in the measuring cell 10 and thus in the exhaust gas to be measured. Because such $NO_x$ sensors are highly dependent on temperature, a heating element 14 ensures that the probe temperature is always kept in a predefined temperature range in order to maintain the necessary measuring accuracy.

A micro-controller 20 is used, in conjunction with an analog circuit 21, to generate a virtual ground as a common reference potential in the center of the supply voltage range. The circuit configuration is illustrated in detail in FIG. 2. A pulse-width-modulated signal which is generated in a PWM (Pulse Width Modulation) unit 22 within the micro-controller 20 is converted into a DC voltage signal using an analog filter circuit 23. In order to obtain a sufficiently low output impedance, an impedance converter 24, for example in the form of a complementary emitter follower or an operational amplifier connected as a buffer amplifier is connected downstream. The output potential of the impedance converter 24 is read into the micro-controller 20 by an A/D converter 25 and is output as an actual value of the virtual ground VM_act to a difference former 26. The difference former 26 determines a difference value ΔVM from the actual value VM_act and a setpoint value VM_setp of the virtual ground. The setpoint value is read out here from a read-only memory (ROM) 27 which is preferably integrated into the micro-controller 20. If a programmable read-only memory, for example an EPROM, is used, it is possible to perform a compensation of asymmetries which may occur, or to perform a restandardization during the service life of the sensor. The difference value ΔVM is fed to a controller 28, for example a PID controller, within the micro-controller 20, that controls the PWM unit 22.

As a result of the use of a micro-controller with an integrated A/D converter or A/D converters, it is possible to read voltage potentials within the circuit configuration and further process them as desired through the use of a difference formation. In this way, it is possible to dispense with an additional analog formation of differences which would result in corresponding tolerance errors. In comparison with a purely analog circuit configuration, the combination of a micro-controller with an analog circuit thus permits to reduce the overall error of the circuit to the errors of the A/D conversion, that is to say the quantization errors and any leakage currents which may occur.

The invention has been described by way of example for a $NO_x$ sensor, but it is to be noted that corresponding circuit configurations are also suitable for other exhaust gas probes which operate according to the principle of the galvanic oxygen concentration cell with a solid electrolyte, for example linear oxygen probes.

We claim:

1. A circuit configuration for generating a virtual ground for an exhaust probe operating according to a principle of a galvanic oxygen concentration cell with a solid electrolyte, comprising:

a micro-controller for determining an actual value of a virtual ground and generating a pulse-width-modulated signal;

an analog circuit connected to said micro-controller, said analog circuit converting the pulse-width-modulated signal into the virtual ground; and a read-only memory operatively connected with said micro-controller for providing a setpoint value of the virtual ground.

2. The circuit configuration according to claim 1, wherein said read-only memory is a programmable read-only memory.

3. The circuit configuration according to claim 1, wherein said read-only memory is integrated into said micro-controller.

4. The circuit configuration according to claim 1, wherein:
said micro-controller includes a difference former, a pulse-width modulation unit, and a controller;
said difference former forms a difference value from the actual value of the virtual ground and the setpoint value of the virtual ground;
said pulse-width modulation unit generates the pulse-width-modulated signal; and
said controller controls said pulse-width modulation unit based on the difference value.

5. The circuit configuration according to claim 4, wherein said controller is a PID controller.

6. The circuit configuration according to claim 1, wherein:
said micro-controller has an output impedance;
said analog circuit includes a filter circuit and an impedance converter;
said filter circuit converts the pulse-width-modulated signal into a DC voltage signal; and
said impedance converter adapts the output impedance of said micro-controller.

7. In combination with an exhaust probe operating according to a principle of a galvanic oxygen concentration cell having a solid electrolyte, a circuit configuration for generating a virtual ground, comprising:
a micro-controller for determining an actual value of the virtual ground and generating a pulse-width-modulated signal;
an analog circuit connected to said micro-controller, said analog circuit converting the pulse-width-modulated signal into the virtual ground; and
a read-only memory operatively connected with said micro-controller for providing a setpoint value of the virtual ground.

8. The circuit configuration according to claim 7, wherein said read-only memory is a programmable read-only memory.

9. The circuit configuration according to claim 7, wherein said read-only memory is integrated into said micro-controller.

10. The circuit configuration according to claim 7, wherein:
said micro-controller includes a difference former, a pulse-width modulation unit, and a controller;
said difference former forms a difference value from the actual value of the virtual ground and the setpoint value of the virtual ground;
said pulse-width modulation unit generates the pulse-width-modulated signal; and
said controller controls said pulse-width modulation unit based on the difference value.

11. The circuit configuration according to claim 10, wherein said controller is a PID controller.

12. The circuit configuration according to claim 7, wherein:
said micro-controller has an output impedance;
said analog circuit includes a filter circuit and an impedance converter;
said filter circuit converts the pulse-width-modulated signal into a DC voltage signal; and
said impedance converter adapts the output impedance of said micro-controller.

13. An exhaust probe configuration, comprising: an exhaust probe having a galvanic oxygen concentration cell configuration with a solid electrolyte;
a circuit configuration connected to said exhaust probe for generating a virtual ground;
said circuit configuration including a micro-controller, an analog circuit and a read-only memory;
said micro-controller determining an actual value of the virtual ground and generating a pulse-width-modulated signal;
said analog circuit converting the pulse-width-modulated signal into the virtual ground; and
said read-only memory providing a setpoint value of the virtual ground.

14. The exhaust probe configuration according to claim 13, wherein said read-only memory is a programmable read-only memory.

15. The exhaust probe configuration according to claim 13, wherein said read-only memory is integrated into said micro-controller.

16. The exhaust probe configuration according to claim 13, wherein:
said micro-controller includes a difference former, a pulse-width modulation unit, and a controller;
said difference former forms a difference value from the actual value of the virtual ground and the setpoint value of the virtual ground;
said pulse-width modulation unit generates the pulse-width-modulated signal; and
said controller controls said pulse-width modulation unit based on the difference value.

17. The exhaust probe configuration according to claim 16, wherein said controller is a PID controller.

18. The exhaust probe configuration according to claim 13, wherein:
said micro-controller has an output impedance;
said analog circuit includes a filter circuit and an impedance converter;
said filter circuit converts the pulse-width-modulated signal into a DC voltage signal; and
said impedance converter adapts the output impedance of said micro-controller .

* * * * *